United States Patent [19]

Haddleton et al.

[11] Patent Number: 5,770,665
[45] Date of Patent: Jun. 23, 1998

[54] FREE RADICAL POLYMERIZATION PROCESS

[75] Inventors: David M. Haddleton, Kenilworth; Andrew V. G. Muir, London; Stephen W. Leeming, Manchester, all of Great Britain

[73] Assignee: Zeneca Limited, London, England

[21] Appl. No.: 663,218

[22] PCT Filed: Dec. 20, 1994

[86] PCT No.: PCT/GB94/02769

§ 371 Date: Aug. 28, 1996

§ 102(e) Date: Aug. 28, 1996

[87] PCT Pub. No.: WO95/17435

PCT Pub. Date: Jun. 29, 1995

[30] Foreign Application Priority Data

Dec. 20, 1993 [GB] United Kingdom .................. 9325950
Oct. 11, 1994 [GB] United Kingdom .................. 9420448

[51] Int. Cl.$^6$ ................. C08F 4/12; C08F 4/80; C08F 20/18; C07F 5/02

[52] U.S. Cl. .......... 526/131; 526/133; 526/328; 526/172; 556/7; 556/138

[58] Field of Search ............... 556/7, 138; 526/131, 526/133, 172, 328

[56] References Cited

U.S. PATENT DOCUMENTS 4,680,354  7/1987  Lin et al. .
4,694,054  9/1987  Janowicz ................................. 526/93
4,722,984  2/1988  Janowicz .
4,746,713  5/1988  Janowicz .
4,886,861  12/1989 Janowicz .
5,010,146  4/1991  Kohsaka .
5,028,677  7/1991  Janowicz .

FOREIGN PATENT DOCUMENTS 199 436  10/1986  European Pat. Off. .

*Primary Examiner*—Thurman K. Page
*Assistant Examiner*—Wu C. Cheng
*Attorney, Agent, or Firm*—Pillsbury Madison & Sutro LLP

[57] ABSTRACT

A compound for effecting molecular weight control in polymerisation is a CoII chelate of formula, wherein each group R is an organic cyclic group which, independently, is a monovalent group which comprises a cyclic structure or taken together as two adjacent groups provides a divalent group, and wherein further at least one of the groups R includes at least one heteroatom selected from 0, N, S, P, halogen and Si, which heteroatom provides a substituent group or part of a substituent group on the cyclic structure, or a heteroatom of a heterocyclic ring of the cyclic structure; and wherein each group Q is independently selected from F, Cl, Br, OH, $C_{1-12}$ alkoxy and $C_{1-12}$ alkyl; or being a CoIII analogue of the cobalt II chelate of formula in which the Co atom is additionally covalently bonded to H, a halide or other anion, or a homolytically dissociable organic group. Free-radical polymerication of at least one ethylenically unsaturated monomer is carried out in the presence of such a compound.

17 Claims, No Drawings

FREE RADICAL POLYMERIZATION PROCESS

The present invention relates to a process for the free-radical initiated polymerisation of olefinically unsaturated monomer(s) in which molecular weight control is achieved by the presence of certain cobalt chelate complexes.

Polymers of low molecular weight, known as oligomers, are often desired for various applications such as coating compositions) either in their own right or as precursors for other polymers. In order to form oligomers it is necessary to control appropriately the polymerisation process being used to yield the desired type of product. In free-radical polymerisations, which are widely used for polymerising olefinically unsaturated monomers, various conventional means are employed for controlling and limiting the molecular weight of the growing polymer chains. Of these, the addition of thiol compounds to the polymerisation has probably been used the most extensively; the thiol acts as an effective chain transfer agent but unfortunately contaminates the system to which it has been added by virtue of its distinctive and persistent odour.

More recently, attention has turned to the use of various transition metal complexes, particularly cobalt chelate complexes, as chain transfer agents for use in controlling molecular weight when radically polymerising olefinically unsaturated monomers.

For example, various literature references, such as N. S. Enikolopyan et al. J. Polym. Sci., Polym. Chem. Ed., Vol 19, 879 (1981), disclose the use of cobalt II porphyrin complexes as chain transfer agents in free radical polymerisation, while U.S. Pat. No. 4,526,945 discloses the use of dioxime complexes of cobalt II for such a purpose. Various other publications, e.g. U.S. Pat. No. 4,680,354, EP-A-0196783, and EP-A-0199436, describe the use of certain other types of cobalt II chelates as chain transfer agents for the production of oligomers of olefinically unsaturated monomers by free-radical polymerisation. WO-A-87/03605 on the other hand claims the use of certain cobalt III chelate complexes for such a purpose.

We have now discovered that molecular weight control in the free-radical polymerisation of olefinically unsaturated monomers may be very effectively achieved with a further class of cobalt chelate complexes which have not been disclosed in the prior art.

According to the present invention there is provided a process for the free-radical polymerisation of olefinically unsaturated monomer(s) (especially methacrylate monomer (s)) using a free-radical initiator, the polymerisation being performed in the presence of a compound for effecting molecular weight control, the molecular weight control compound being a CoII chelate of the following formula I:

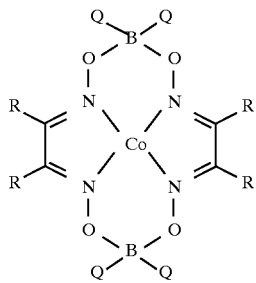

wherein each group R is an organic group which, independently, is a monovalent group which comprises a cyclic structure, or taken together as two adjacent groups provides a divalent group completing a cyclic structure comprising a first cyclic ring containing the said adjacent carbon atoms and optionally including a second cyclic ring, and wherein further one or more of the groups R includes at least one heteroatom selected from O, N, S, P, halogen and Si, which heteroatom provides a substituent group or part of a substituent group on the cyclic structure, or a heteroatom of a heterocyclic ring of the cyclic structure; and wherein each group Q is independently selected from F, Cl, Br, OH, $C_{1-2}$ alkoxy and $C_{1-2}$ alkyl; or being a CoIII analogue of the cobalt II chelate of formula I in which the Co atom is additionally covalently bonded, usually in a direction at rights angles to the macrocyclic chelate ring system, to H, a halide or other anion, or a homolytically dissociable organic group; see WO-A-87/03605 for compounds of such a CoIII chelate type.

The groups R may, independently, be monovalent groups of aromatic or aliphatic character, or may have a combination of aromatic and aliphatic character. Adjacent groups R and R taken together may also provide a divalent group, preferably having or including a cyclic structure (i.e. a structure which has or includes one or more rings) which can be of aromatic or cycloaliphatic character or a combination of aromatic and cycloaliphatic character.

The groups Q are preferably all the same and more preferably are all F.

The defined Co chelates are found to be very effective as molecular weight control compounds; also the presence of the heteroatom(s) may in many cases allow one to control the solubility of the chelates in an organic or aqueous polymerisation medium, some chelates, e.g. in comparison to analogous compounds lacking the heteroatom(s) or the substituent(s) comprising the heteroatom(s), exhibiting enhanced solubility or decreased solubility in an aqueous or organic medium. Additionally, the use of the defined Co chelates in suspension polymerisation allows the incorporation of glycidyl methacrylate into the oligomers. This monomer is incompatible with thio-containing chain transfer agents owing to the reaction of the epoxide ring.

In one embodiment of the invention the Co chelate more specifically has the following formula II:

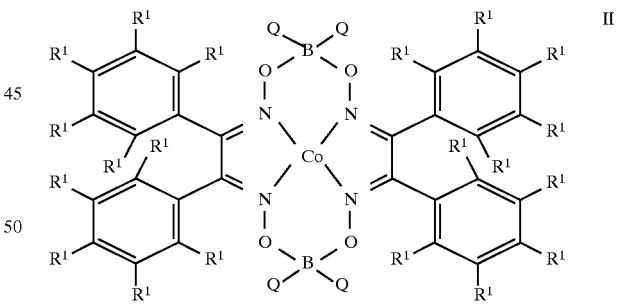

wherein the groups $R^1$ are each independently selected from hydrogen, $C_{1-12}$ alkyl (preferably methyl), optionally substituted $C_{6-10}$ aryl (preferably phenyl), OH, $OR^2$ [where $R^2$ is $C_{1-12}$ alkyl (preferably methyl) or $(CH_2-CH_2-O-)_nT$ where n is 1 to 40 and T is H or a capping group selected from $C_{1-10}$ alkyl, $C_{2-11}$ acyl and (meth)acryloyl], $NH_2$, $NHR^2$, $NR^2_2$, $SO_3H$, $SO_3M$ (where M is a cationic group, for example an alkali metal or ammonium radical), $SO_3R^2$, $SO_2NH_2$, $SO_2NHR^2$, $CO_2H$, $CO_2R^2$, $NO_2$, CN, C(=O)H, $C(=O)R^2$, halogen (preferably Cl, Br, I or F), SH, $SR^2$, 2-furyl, and 3-furyl, provided that at least one of the $R^1$ groups, and preferably at least one $R^1$ group of at least two of the aromatic rings (more preferably of each aromatic ring), is selected from OH, $OR^2$, $NH_2$, $NHR^2$, $NR^2_2$, $SO_3H$, $SO_3M$, $SO_3R^2$, $SO_2NH_2$, $SO_2NHR_2$, $CO_2H$, $CO_2R^2$, $NO_2$, CN, C(=O)H, C(=O)$R^2$, halogen, SH, $SR^2$, 2-furyl and 3-furyl, wherein $R^2$ and M are as defined above, and wherein further one or preferably both pairs of opposing 6-positioned $R^1$ groups may also represent a direct bond, so that formula II then reduces to a cobalt chelate of the following formula III

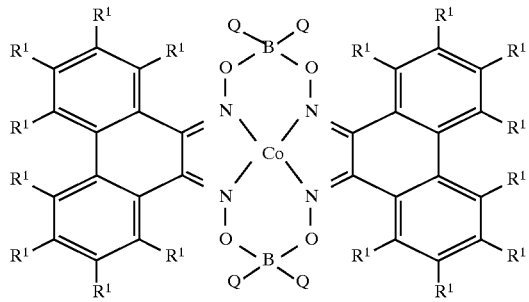

wherein $R^1$ and Q are as defined supra.

It is preferable in the compounds of formulae II and III for one $R^1$ group of each of at least two of the aromatic rings, and more preferably of each aromatic ring, to be a heterosubstituent selected from OH, $OR^2$, $NH_2$, $NHR^2$, $NR^2_2$, $SO_3H$, $SO_3M$, $SO_3R^2$, $SO_2NH_2$, $SO_2NHR^2$, $CO_2H$, $CO_2R^2$, $NO_2$, CN, C(=O)$R_2$, halogen, SH, $SR^2$, 2-furyl, and 3-furyl, with the remaining $R^1$ groups in each heterosubstituted ring being hydrogen (apart from when they provide direct bonds as in formula III) and where, in any aromatic ring having no heterosubstituent as defined, all the groups $R^1$ are hydrogen (except when providing a direct bond). Particularly preferably, at least two rings have a heterosubstituent in the 4-position, with the remaining $R^1$ groups in the heterosubstituted rings being hydrogen and all the $R^1$ groups being hydrogen in a non-heterosubstituted ring, such a chelate having the following formula IV:

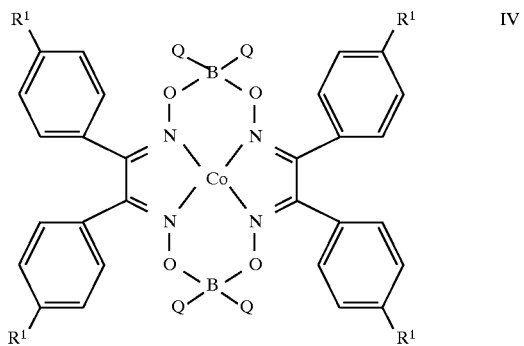

where each of at least two $R^1$ groups is a heterosubstituent as defined above (preferably all four $R^1$ groups) and if $R^1$ is not a heterosubstituent it is hydrogen, and Q is as defined supra. In such a formula, $R^1$ may for example be $NO_2$, $OCH_3$, halogen (especially Br), $SO_3H$, or $SO_3CH_3$ (or hydrogen in one or two of the rings). Q is preferably F. In most cases when $R^1$ is a heterosubstituent in two or more rings, it will be the same heterosubstituent. Especially preferred are compounds of the formula (IV) in which each of at least two $R^1$ groups is selected from $NO_2$, halogen, methoxy and $SO_3H$ and Q is F. Even more preferably each of the $R^1$ groups selected from $NO_2$, halogen, methoxy and $SO_3H$ is substituted at the 4-position. Specific such compounds which we have found may give excellent results are those in which all $R^1$ groups are each selected from $NO_2$, halogen and methoxy and that in which two of the $R^1$ groups are each $SO_3H$ and the remainder are each H.

In another preferred embodiment of the invention, the Co chelate has the following formula V:

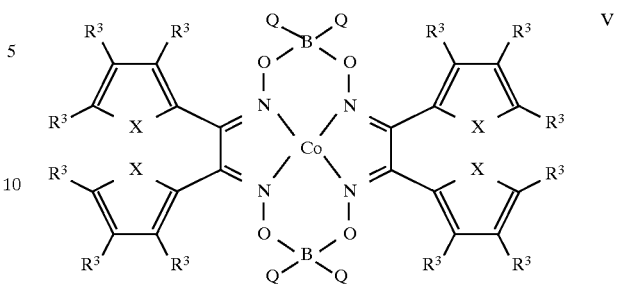

or corresponding compounds in which one or more (or all) of the 5-membered ring groups are joined at the 3 position instead of the 2 position (as shown above in V) in which case $R^3$ is attached to a 2-position; and wherein each $R^3$ is selected, independently, from hydrogen, $C_{1-12}$ alkyl (preferably methyl), optionally substituted $C_{6-10}$ aryl (preferably phenyl), OH, $OR^2$ (preferably $OCH_3$), $NH_2$, $NHR^2$, $NR^2_2$, $SO_3H$, $SO_3M$, $SO_3R^2$, $SO_3NH_2$, $SO_2NHR^2$, $CO_2H$, $CO_2R^2$, $NO_2$, CN, C(=O)H, C(=O)$R^2$, halogen (preferably Cl, Br, I or F), SH, and $SR^2$, but is preferably $C_{1-4}$ alkyl or methoxy and more preferably hydrogen; and wherein X is selected, independently from O, S, NH and $NR^4$ where $R^4$ is $C_{1-8}$ alkyl, $C_{6-10}$ aryl (preferably phenyl) or $C_{6-10}$ cycloalkyl (preferably cyclohexyl). Q is as defined above, and is preferably F.

It is particularly preferred that the chelate of formula V has each $R^3$=hydrogen, each Q=F, and each X=oxygen, the resulting compound having the following

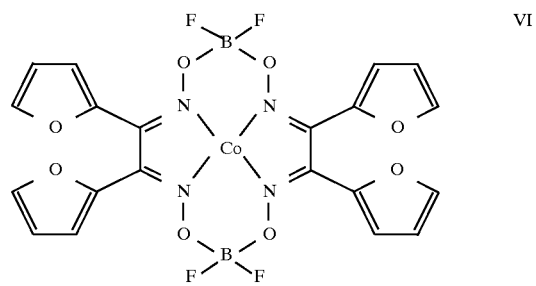

For the sake of clarity, it is confirmed that by a "2- furyl" group herein is meant the group of formula

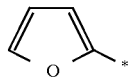

With respect to the various alkyl groups defined supra, they may be straight chained or branched where the option arises.

As mentioned above many of the chelates show enhanced or decreased solubility in aqueous or organic media, allowing one to readily control the solubility of the catalyst in the polymerisation medium. For example, many of the —$SO_3$ substituted compounds show enhanced solubility in water and methanol while many —Br, —$OCH_3$ and —$NO_2$ substituted chelates show reduced solubility in water and methanol.

With regard to the CoIII analogues of the compounds of formulae I to VI these arise when the Co is additionally bonded to a further atom, ion or organic group which is homolytically dissociable, such as H, optionally substituted $C_{1-12}$ alkyl, cyano, halide, ester, $C_{6-10}$ aryl (including heterocyclic $C_{6-10}$ aryl), and alicyclyl (including heterocyclic $C_{6-10}$ alicyclyl) such a further group usually being located in an axial position (i.e. perpendicular to the equatorial ligands as shown in the formulae I to VI). Alkyl groups bearing one or more substituents on the carbon atom bonded to the metal ion are particularly suitable; such substituents may include nitrile, ester, and optionally substituted aromatic groups. Some of these CoIII complexes may be stable materials under ordinary storage conditions, and may only react under the free-radical-generating conditions of the polymerisation process. Others, particularly where H is the further (axial) group, may be highly reactive intermediate species —and indeed it is possible that all the CoII complexes (and possibly the CoIII ones as well) exert their chain transfer effect by proceeding through the reactive COIIIH intermediate. It is also possible that there is always a periodic interchange between the CoII and CoIII valency states in the complexes during the polymerisation. In fact the actual mechanism of involvement is complex and not properly understood on our part and we do not wish to be bound by any particular theory nor to an identification of the specific chemical constitution or valency state of the Co complex during the actual polymerisation process.

It is also possible for the cobalt complexes as defined supra (i.e. CoII or CoIII complexes) additionally to have further ligands coordinated to the Co atom (presumably axially), which do not alter the Co valency state. These may be derived en passant from the reaction medium used in the preparation of the Co complex or from the polymerisation medium used in the polymerisation process, or may be derived by deliberately adding a compound which will provide such ligands, and it is often the case that the coordinated presence thereof in the complex will ameliorate the latter's effectiveness. However, they are not essential to the invention, and for convenience they have not been shown in the various formulae. Typical of such additional ligands are weakly basic tertiary amines such as pyridine (or their substituted derivatives), trialkyl amines, dialkylamines, ethers such as tetrahydrofuran and diethyl ether, alkanols such as methanol, and also optionally substituted trialkyl, triaryl or tri(alkyl/aryl) phosphines (or analogous compounds such as corresponding alkoxy or aryloxy phosphines). (The alkyl groups mentioned above preferably, and independently, are of 1–14 carbons and the aryl groups preferably, and independently, are of 6–10 carbons, more preferably phenyl). One or more water molecules could also be coordinated to the Co complex.

The Co chelates of the invention are electrically neutral, the surrounding ligands providing a double negative charge to balance the $Co^{2+}$ charge. The negative charges are believed to be delocalised rather than being on any particular atoms.

The defined cobalt chelate complexes allow the efficient production of oligomers and are likely to be functioning as catalytic chain transfer agents (CCTAs), and are sometimes referred to as such in this specification. Generally speaking, the degree of polymerisation of such oligomers (overall in the case of copolymers) will usually be within the range 2 to about 1000 (i.e. 2 to 1000 polymerised units), preferably 10 to 750, and more preferably 10 to 130.

The polymerisation process can be carried out in the presence of a polymerisation medium (acting as a carrier medium for the components and as a heat transfer medium) or in the absence of such a medium (i.e. in bulk). When using a polymerisation medium, the polymerisation may be e.g. a solution, suspension or emulsion polymerisation.

Typical organic solvents which may be used as the medium for the polymerisation include aromatic hydrocarbons such as benzene, toluene, and the xylenes; ethers such as diethyl ether, tetrahydrofuran, alkoxylated ethylene glycol or polyethyleneglycol; alcohols such as methanol, ethanol, propanol and butanol and their esters with carboxylic acids such as acetic, propionic and butyric acids; ketones such as acetone or methyl ethyl ketone; and liquid tertiary amines such as pyridine. Mixtures of solvents may be used. Water may also be used as a polymerisation medium (sometimes in combination with a solvent(s) such as described above) as in suspension or emulsion polymerisations, and for such processes conventional emulsifying or suspension agents may be employed. When conducting emulsion polymerisation, emulsifiers which may be used are non-ionic or anionic surfactants such as the Na, K and ammonium salts of dialkylsulphosuccinates, Na, K and ammonium salts of sulphonated oils, Na, K and $NH_4$ salts of fatty acids. However, cationic emulsifiers such as hexadecyltrimethyl ammonium bromide and nonionic surfactants based on e.g. ethoxylated compounds may also be used. The amount used is usually 0.2 to 15% by weight, preferably 0.2 to 5% by weight based on the total monomer(s) charged. Suspension polymerisation may employ as stabilisers protective colloids such as partially hydrolysed polyvinyl acetate (various degrees of hydrolysis), cellulose derivatives, gelatin, polyvinyl chloride, and polyacrylic acid. The amount used is usually 0.1 to 8%, calculated on monomer weight. Salts such as $Na_2SO_4$ are also often included for reducing monomer solubility in the aqueous phase and to improve stabilisation. The polymerisations are usually performed at a temperature within the range of 25° to 160° C. (more usually 45° to 90° C.). Any suitable free radical yielding initiator appropriate to the type of polymerisation system being employed may be used in the process of the invention, the usual criteria being that it has acceptable solubility in one or more of the other polymerisation components (e.g. solvent, monomers, or water), is sufficiently active at the polymerisation temperature (usually having a half life within the range 0.5 to 5 hours), and does not unacceptably affect the stability of the Co chelate. Examples of such free-radical-yielding initiators include azo compounds as 2,2'-azobis(isobutyronitrile), 2,2'-azobis-(2-methyl)butanenitrile,4,4'-azobis(4-cyanovaleric acid), 2-(t-butylazo)-2-cyanopropane, 2,2'-azobis[2-methyl-N-(1,1)-bis(hydroxymethyl)-2-hydroxethyl]-propionamide, and 2,2'-azobis[2-methyl-N-hydroxyethyl)]-propionamide. Other soluble free radical initiators may also be used, examples of which include peroxy compounds such as benzoyl peroxide, lauroyl peroxide, hydrogen peroxide, and Na, K, and $NH_4$ persulphates. Redox initiator systems can also be used, examples of which include redox pairs such as $NH_4$ persulphate and Na metabisulphite.

The use of the defined Co chelates as molecular weight control compounds in the invention process avoids the requirement to use conventional chain transfer agents which often have disadvantages of one sort or another. For example, mercaptans impart a pronounced odour, while halogenated hydrocarbons (such as bromoform or carbon tetrachloride) are environmentally suspect. α-Methyl styrene (another known chain transfer agent), on the other hand, possibly in combination with styrene itself, is considerably more expensive than methyl methacrylate and often has to be used at very high levels, e.g. up to 35 weight % (although its deliberate use as a comonomer is not of course precluded; similarly the use of styrene itself as a comonomer is not precluded).

The defined Co chelate, acting to control molecular weight, may be used in a low amount (because it acts in a catalytic manner) in comparison to conventional chain transfer agents for achieving comparable molecular weight reduction. This allows much purer product to be made.

Moreover, the defined Co chelate is, if an appropriate solubilising hetero-containing group is chosen, in particular, unexpectedly effective in suspension polymerisations in that it is not necessary to employ high levels of suspension agents (for stabilisation). We believe this not to be the case for known Co metal chelate compounds described in the above-discussed prior art such as EP-A-0199436 (which discloses the use of $BF_2$-bridged cobaloxime chelates not having heteroatom-containing substituents as defined herein as molecular weight control compounds in free-radical polymerisation) wherein in our experience uneconomically high concentrations of suspension agents are required for stabilisation in order to ensure effective use of the catalyst. In particular, the amount of suspending agent used in the general procedure for suspension polymerisation disclosed in EP-A-0199436 is equivalent to about 15 g per 100 g of monomer. In contrast, we find surprisingly that efficient stabilization can be achieved using a CCTA in accordance with the invention and a suspending agent in an amount of as little as up to 8 g per 100 g of monomer, more preferably from 0.1 to 5 g, especially 2 to 4 g, per 100 g monomer. In short, we find surprisingly that, even with such reduced amounts of suspending agent, excellent results both in terms of stability and effective catalytic activity can be achieved for suspension polymerisation using as little as at least 5 times less than the amount used in the process of EP-A-0199436.

The invention process may be carried out using an "all-in-one" batch process in which all components are present in the reaction medium at the start of polymerisation or a semi batch process in which one or more the components employed (usually at least one of the monomers) is wholly or partially fed to the polymerisation medium during the polymerisation.

The chelates used in the process may be prepared beforehand or may be formed in-situ from the appropriate reactants. Typically the level of the cobalt chelate used in the polymerisation process will be such that the ratio of monomer(s)/initiator (molar basis) is within the range of from 20 to 500, more usually 40 to 300. Also typically, the level of cobalt employed will be such that the ratio of cobalt chelate to free-radical initiator (molar basis) is often within the range of 0.001 to 0.1, more usually 0.003 to 0.08. Also typically, the molar ratio of monomer(s) to cobalt chelate will often be in the range of from 5,000/1 to 2,000,000/1.

The process of the invention is most effectively applied to the homo-or copolymerisation of methacrylate esters and styrenes, although acrylate esters can also be polymerised effectively if included as comonomers.

Examples of monomers that may be polymerised include methyl methacrylate, ethyl methacrylate, butyl methacrylate (all isomers), and other alkyl methacrylates (usually up to 14 carbons); corresponding acrylates; also functionalised methacrylates and acrylates including glycidyl methacrylate, trimethoxysilyl propyl methacrylate, allyl methacrylate, hydroxyethyl methacrylate, hydroxypropyl methacrylate, dialkylaminoalkyl methacrylates; fluoroalkyl (meth) acrylates; methacrylic acid, acrylic acid; fumaric acid (and esters), itaconic acid (and esters), maleic anhydride; styrene, α-methyl styrene; vinyl halides such as vinyl chloride and vinyl fluoride; acrylonitrile, methacrylonitrile; vinylidene halides of formula $CH_2=C(Hal)_2$ where each halogen is independently Cl or F; optionally substituted butadienes of the formula $CH_2=C(R^8) C(R^8)=CH_2$ where $R^8$ is independently H, $C_{1-10}$ alkyl, Cl, or F; sulphonic acids or derivatives thereof of formula $CH_2=CHSO_2OM$ wherein M is Na, K, Li, $N(R^9)_4$, H, $R^9$ or $—(CH_2)_2$-D where each $R^9$ is independently H or $C_{1-10}$ alkyl, D is $CO_2Z$, OH, $N(R^9)_2$ or $SO_2OZ$ and Z is H, Li, Na, K or $N(R^9)_4$; acrylamide or derivatives thereof of formula $CH_2=CHCON(R^9)_2$, and methacrylamide or derivates thereof of formula $CH_2=C(CH_3)CON(R^9)_2$. Mixtures of such monomers may be used.

Preferred monomers are $C_{1-10}$ alkyl methacrylates and acrylates, hydroxy $C_{1-14}$ alkyl methacrylates and acrylates, epoxy $C_{1-14}$ alkyl methacrylates and acrylates, methacrylic acid, styrene and styrene derivatives.

The present invention is now illustrated but in no way limited by reference to the following examples. Unless otherwise specified all parts, percentages and ratios are on a weight basis.

GENERAL PROCEDURES (i) Solution Polymerisation

To a 200 ml Schlenk tube filled with dry nitrogen and 0.085 g AIBN (2,2' azoisobutyronitrile, recrystallised from ethanol) were added the appropriate amounts of the monomers (typically 10 ml methyl methacrylate, MMA) and 20 ml of the appropriate solvent, all of which had been previously sparged with dry nitrogen. The desired amount of cobalt catalyst was then added and the tube heated at 60° C. under nitrogen.

(ii) Suspension Polymerisation 400 g of distilled water, 0.6 g sodium sulphate and 2.4 g HX39 stabiliser (polyacrylic acid) were degassed with nitrogen for 1 hour and charged to a reactor. A solution of 100 g degassed methyl methacrylate containing 1.25 g AIBN and the appropriate amount of cobalt catalyst was then added and the reaction stirred at 500 rpm in a reactor inside a water bath at 80° C. under nitrogen for 3 hours.

Typical Preparations of Dioximes

Preparation of 4,4'-dinitrobenzil dioxime 4,4'-dinitro benzil (5 g; 0.017 mols) and hydroxylamine hydrochloride (3.5 g; 0.05 mols) were stirred together in ethanol (75 cm³). After stirring at ambient temperature for 20 minutes, potassium acetate (5 g; 0.051 mols) was added and the mixture heated with stirring. The mixture was heated under reflux for 18 hours, then filtered whilst still hot. The filtrate was discarded. The insoluble material was washed with deionised water (3×50 cm³) to remove any inorganics present to yield an off-white powdery solid. Yield=0.7 g; 0.002 mols; 11.8%). Results of micro analysis: %Th(found): C 50.9, (50.5); H 3.0, (3.6); N 17.0, (15.8); for $C_{14}H_{10}N_4O_6$.

Preparation of Benzildioxime-4-sulphonic acid

Benzil-4-sulphonic acid (23.2 g; 0.080 mols); hydroxylamine hydrochloride (17.10 g; 0.25 mols) and sodium carbonate (9.08 g; 0.086 mols) were stirred together in water (200 cm³). A yellow solution was formed and effervescence was observed. The clear solution was heating with stirring until reflux temperature (102° C.) was obtained. The mixture was heated under reflex for 90 minutes. During this reflux period the colour of the solution slowly changed to pink. The mixture was cooled to ambient temperature and the pH adjusted with hydrochloric acid (3 cm³ of 30% (w/v)) until it reached 2. A white solid precipitate was formed. This was removed by filtration, dried at ambient temperature in vacu. to yield 17.5 g; 0.055 mols; 68.8%. Micro analysis: %Th (found) C 49.1, (49.0); H 3.2, (3.2); N 8.2, (8.5); S 9.4, (9.2) for $C_{14}H_{11}N_2O_5SNa$.

Preparation of 4.4'-dimethoxvbenzil dioxime

This material was prepared according to J. Chemical Society (1925), 125, 2874. 4.0 g sodium hydroxide pellets, 25 cm$^3$ water, 2.0 g hydroxlamine hydrochloride, 2.7 g 4,4'-dimethoxy benzil, 4 drops ethanol. Yield=0.9 g; Mpt 214° C. (uncorr). Micro analysis: %Th(found) C 64.0, (63.9); H 5.3, (5.9); N 9.3 (8.9), for $C_{16}H_{16}N_2O_4$.

Preparation of 4,4'-dibromobenzil dioxime 4,4'-dibromo benzil (3.68 g; 0.01 mols); potassium acetate (7.84 g; 0.08 mols) and hydroxylamine hydrochloride (2.78 g; 0.04 mols) were stirred together with ethanol (150 cm$^3$). The mixture was heated under reflux (78° C.) for 3 hours. A pink solution was formed during this reflux period. The mixture was screened hot and the filtrate concentrated to yield a pink (needle) crystalline solid. Yield=1.67 g; 0.004 mols; 44.2%.

Micro analysis: %Th(found) C 42.2 (42.3), H 2.5 (2.5); N 7.0 (7.0); Br 40.2 (39.2) for $C_{14}H_{10}N_2O_2Br_2$.

Typical Preparations of cobalt complexes
Cobalt complex of 4,4'-dimethoxvbenzil dioxime Cobalt acetate 0.4 H$_2$O (0.75 g; 0.0030 mols) was dissolved in methanol (30 cm$^3$). The mono sodium salt of 4,4'-dimethoxy benzil dioxime (2.0 g; 0.0062 mols) was added and the mixture stirred at ambient temperature. A bright red crystalline precipitate (needle) was formed. The mixture was stirred for 100 minutes and then filtered. The solid was washed with methanol (20 cm$^3$) and then pumped to dryness. Diethyl ether (30 cm$^3$) was added followed by boron trifluoride etherate (20 cm$^3$). A red solution was formed, momentarily, at this point then (within 2 minutes) a red/orange precipitate was observed. The mixture was stirred for a further 1 hour and then filtered. The solid obtained was washed with diethyl ether (3×15 cm$^3$), water (35 cm$^3$) and finally methanol (35 cm$^3$). The resulting dark red solid was pumped to dryness. Yield=1.5 g. Micro analysis: %Th(found) C 49.9, (50.1); H 4.4, (5.1), N 6.9, (6.9); B 2.7, (2.3); Co 7.2, (6.9) for $C_{32}H_{28}N_4O_8B_2F_4Co$. 2MeOH Cobalt complex of 4,4'-dibromobenzil dioxime Cobalt acetate 0.4 H$_2$O (0.65 g; 0.0026 mols) was stirred in solution with methanol (10 cm$^3$). 4,4'-dibromo benzil dioxime (1.7 g; 0.0043 mols) was added with stirring. A dark precipitate was formed. The mixture was stirred for 45 minutes and then filtered. The dark pink solid obtained was pumped to dryness. Diethyl ether (10 cm$^3$) was added followed by boron trifluoride etherate (15 cm$^3$). The mixture was stirred for 45 minutes and then filtered. The resulting solid was washed with ice cold diethyl ether (2×10 cm$^3$), ice cold methanol (10 cm$^3$), water (10 cm$^3$), ice cold methanol (10 cm$^3$) and finally ice cold diethyl ether (10 cm$^3$). The solid was then pumped to dryness to yield a pale pink solid, 1.45 g.

Micro analysis: %Th(found) C 35.5, (34.4); H 2.4, (2.3); N 5.5, (5.5); B 2.2, (2.0); Co 5.8, (5.8) for $C_{28}H_{16}N_4O_4Br_2F_4Co$. 2MeOH.

The other cobalt oxime complexes were prepared according to a similar procedure.

Examples 1 to 4

Solution Polymerisation of MMA in methylethyl ketone (MEK) using cobalt (difurildioxime-diboronfluoride) as a catalytic chain transfer agent Cobalt alpha furildioxime-diboronfluoride (formula VI) was synthesised by the reaction of alpha-furildioxime (2 mole equivalent), cobalt acetate tetrahydrate (1 mole equivalent) and BF$_3$OEt$_2$ (10 mole equivalent) in degassed diethyl ether. The general procedure for solution polymerisation was followed and the results are detailed in Table 1 below. [MMA]/[Co] means the mole ratio of MMA to Co catalyst. Molecular weights were measured after 1 hr. reaction time.

TABLE 1

| Example | [MMA]/[Co] | Mn | Mw/Mn |
|---------|-----------|-------|-------|
| 1 | 150,000 | 2,300 | 2.22 |
| 2 | 200,000 | 3,322 | 2.3 |
| 3 | 250,000 | 3,470 | 2.3 |
| 4 | 300,000 | 4,065 | 2.4 |

In the absence of catalyst, Mn was typically 55000 and Mw/Mn 2.0.

Example 5

Suspension Polymerisation of MMA using cobalt (difurildioxime-diboronfluoride) as a catalytic chain transfer agent The catalyst was synthesised as described above. The general procedure for suspension polymerisation described above was followed, with the ratio of MMA to the cobalt catalyst being 2000:1 w/w. The results were as follows: Mw=14220, Mw/Mn=2.0. In the absence of any catalyst, molecular weights were >100,000.

Examples 6–17

Use of various defined complexes in the solution polymerisation of methyl methacrylate In all cases the general procedure for solution polymerisation was followed. The experimental results are shown in Table 2 below. Here [Monomer]/[Catalyst] is the molar ratio of monomer to catalyst, molecular weights are reported after 1 hour (measured by gel permeation chromatography GPC against PMMA standards in tetrahydrofuran (THF). The structures of the complexes are also shown in Table 2.

TABLE 2

| Example No | Catalyst | [Monomer]/[Catalyst] | Solvent | Mn | Mw/Mn |
|------------|----------|----------------------|---------|------|-------|
| 6 | Form IV, each Q = F, each R$_1$ = NO$_2$ | 200,000 | THF | 3,736 | 2.3 |
| 7 | " | 300,000 | " | 5,662 | 2.4 |
| 8 | " | 400,000 | " | 7,984 | 2.4 |
| 9 | Form IV, each Q = F, each R$^1$ = Br | 200,000 | THF | 5,418 | 1.8 |
| 10 | " | 300,000 | " | 6,998 | 2.1 |
| 11 | " | 400,000 | " | 8,475 | 2 |
| 12 | Form IV, each Q = F, each R$^1$ = CH$_3$O | 200,000 | THF | 3,349 | 1.9 |
| 13 | " | 300,000 | " | 4,100 | 2 |
| 14 | " | 400,000 | " | 5,297 | 2.3 |
| 15 | Form IV, each Q = F, top R$^1$'s resp. SO$^3$H and H, bottom R$^1$'s H and SO$_3$H* | 50,000 | MeOH | 938 | 1.6 |
| 16 | " | 100,000 | " | 1,705 | 2.9 |
| 17 | " | 250,000 | " | 3,444 | 2.9 |

*going from left to right as per the formula.

In the absence of any catalyst, the molecular weight (Mn) was typically 60,000.

Examples 18–27

Modifications to Examples 6–14

The general procedure used was exactly as for the general procedure for solution polymerisation already described, except that either (1) in the examples in Table 3 below with cobalt (4,4'dimethoxybenzildioximediborondifluoride) and cobalt (4,4'dibromobenzildioximediborondifluoride) as the chain transfer agent the stock solution of the catalyst was made up (roughly 0.2 mM) in methyl methacrylate (MMA) rather than in the solvent used for the reaction, or (2) in the examples in Table 3 below with cobalt (4,4'dinitrobenzildioxime) as the chain transfer agent the catalyst was added directly as a solid to a solution of monomer, initiator and solvent. All examples are with MMA and are at 60° C. in methylethylketone (MEK).

TABLE 3

| Example | Catalyst | [Monomer]/ [Catalyst] | Mn | Mw/Mn |
|---|---|---|---|---|
| 18 | Form IV, each Q = F; R¹ = Br | 1,000,000 | 6,820 | 2.2 |
| 19 | " | 800,000 | 5,388 | 2.1 |
| 20 | " | 600,000 | 3,808 | 2.7 |
| 21 | " | 400,000 | 3,154 | 2 |
| 22 | Form IV, each Q = F; R¹ = OCH₃ | 1,000000 | 7,262 | 2.1 |
| 23 | " | 800,000 | 5,402 | 2 |
| 24 | " | 600,000 | 4,114 | 1.9 |
| 25 | " | 400,000 | 2,186 | 1.9 |
| 26 | Form IV, each Q = F; R¹ = NO₂ | 100,000 | 2,266 | 1.6 |
| 27 | " | 50,000 | 1,352 | 1.3 |

Examples 28–38

Use of various defined complexes in suspension polymerisation

The general procedure for suspension polymerisation was followed except that 100 g of methyl methacrylate were replaced by 100 g of a monomer mixture in Examples 29–32, 34 and 36–38 in Table 4 below (monomer composition being indicated in brackets as weight percent). Results are shown in Table 4 below, structures of the complexes are as given above. Molecular weights were measured by GPC against polystyrene standards in THF after isolation of the beads at the end of the reaction by filtration. MAA is methacrylic acid, BA is n-butyl acrylate.

TABLE 4

| Example | Catalyst | Catalyst/g | Monomer | Mn | Mw/Mn |
|---|---|---|---|---|---|
| 28 | Form IV, each Q = F, each R¹ = NO₂ | 0.02 | MMA | 14,970 | 3.7 |
| 29 | " | 0.02 | MMA (96)/ MAA (4) | 24,080 | 2.8 |
| 30 | " | 0.02 | MMA (92)/ MAA (8) | 20,610 | 2.8 |
| 31 | " | 0.02 | MMA (80)/ BA (20) | 45,170 | 2.9 |
| 32 | " | 0.02 | MMA (60)/ MAA (40) | 70,500 | 5.8 |
| 33 | Form IV, each Q = F, each R¹ = Br | 0.01 | MMA | 24,160 | 2.7 |
| 34 | " | 0.01 | MMA (92)/ MAA (8) | 15,970 | 2.5 |
| 35 | Form IV, each Q = F, each R¹ = CH₃O | 0.01 | MMA | 3,481 | 2.4 |
| 36 | " | 0.01 | MMA (92)/ MAA (8) | 3,205 | 2 |
| 37 | Form VI | 0.05 | MMA (71.8)/ BA (28.2) | 10,762 | 2.53 |
| 38 | " | 0.03 | MMA (96)/ MAA (4) | 19,870 | 3 |

In the absence of any catalyst, the Molecular weights were than 100000.

We claim:

1. A process for the free-radical polymerization of at least one olefinically unsaturated monomer in the presence of a compound for effecting molecular weight control, wherein the molecular weight control compound is a CoII chelate of the following formula I:

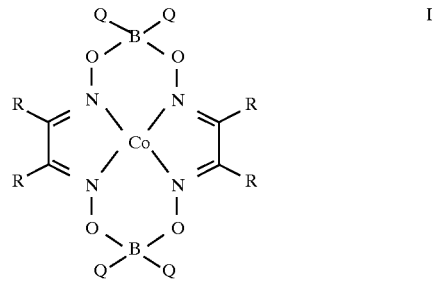

wherein each group R is an organic group and each group R is the same organic group as each other group R, which group R is selected from (a) the group

wherein $R^1$ is a $C_{1-12}$ alkoxy group; and (b) the group

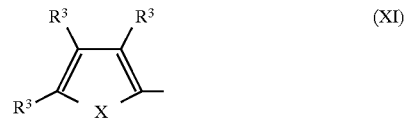

or corresponding compounds in which at least one of the 5-membered ring groups is joined at the 3 position instead of the 2 position (as shown above in XI) in which case $R^3$ is attached to a 2-position;

wherein each $R^3$ is selected independently, from hydrogen, $C_{1-12}$ alkyl, optionally substituted $C_{6-10}$ aryl, OH, $OR^2$, $NH_2$, $NHR^2$, $NR^2_2$, $SO_3H$, $SO_3M$ where M is a cationic radical, $SO_3R^2$, $SO_2NH_2$, $SO_2NHR^2$, $CO_2H$, $CO_2R^2$, $NO_2$, CN, $C(=O)H$, $C(=O)R^2$, halogen, SH, and $SR^2$, wherein $R^2$ is a $C_{1-12}$ alkyl or $(CH_2CH_2-O-)nT$ where n is 1 to 40 and T is H or a capping group selected from $C_{1-10}$ alkyl, $C_{1-1}$ aryl and (meth)acryloyl and wherein each X is selected, independently from 0, S, NH and $NR^4$ where $R^4$ is $C_{1-6}$ alkyl, $C_{6-10}$ aryl or $C_{6-10}$ cycloalkyl, and each group Q is independently selected from F, Cl,. Br, OH, $C_{1-12}$ alkoxy and $C_{1-12}$ alkyl.

2. A process according to claim 1, wherein each Q is F.

3. A process according to claim 1, wherein each group R is a group of the formula (X), given and defined in claim 1 and each $R^1$ is a $C_{1-2}$ alkoxy group.

4. A process according to claim 1, wherein the CoII chelate has the formula IV:

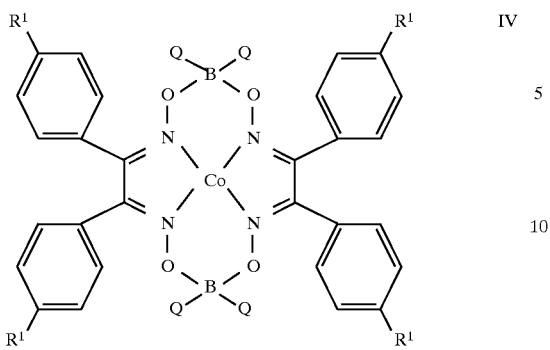

wherein each $R^1$ and each Q is as defined in claim 1.

5. A process for the free-radical polymerization of at least one olefinically unsaturated monomer in the presence of a compound for effecting molecular weight control, wherein the molecular weight control compound is a CoII chelate of the formula

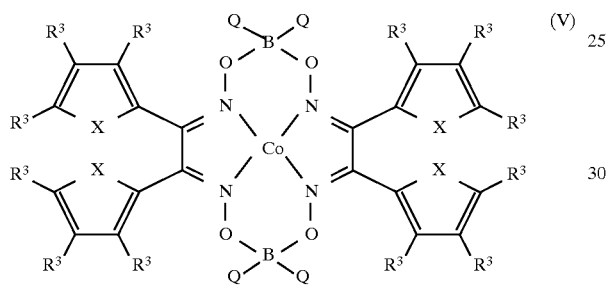

or corresponding compounds in which at least one of the 5-membered ring group is joined at the 3-position instead of the 2-position (as shown above in V) in which case $R^3$ is attached to a 2-position;

wherein each $R^3$ is selected, independently, from hydrogen, $C_{1-12}$ alkyl, optionally substituted $C_{6-10}$ aryl, OH, $OR^2$, $NH_2$, $NHR^2$, $NR^2_2$, SO H, $SO_3M$ where M is a cationic radical, $SO_3R^2$, $SO_2NH_2$, $SO_2NHR^2$, $CO_2H$, $CO_2R^2$, $NO_2$, CN, C(=O) H, C(=O) $R^2$, halogen, SH, and $SR^2$, wherein $R^2$ is a $C_{1-12}$ alkyl or $(CH_2CH_2-O-)nT$ where n is 1 to 40 and T is H or a capping group selected from $C_{1-10}$ alkyl, $C_{1-11}$ aryl and (meth)acryloyl and wherein each X is selected, independently from O, S, NH and $NR^4$ where $R^4$ is $C_{1-6}$ alkyl, $C_{6-10}$ aryl or $C_{6-10}$ cycloalkyl, and wherein each group Q is independently selected from F, Cl, Br, OH, $C_{1-12}$, alkoxy and $C_{1-12}$ alkyl; or being a CoIII analogue of the cobalt II chelate of formula I in which the Co atom is additionally covalently bonded to H, a halide or other anion, or a homolytically dissociable organic group.

6. A CoII chelate of the following formula I:

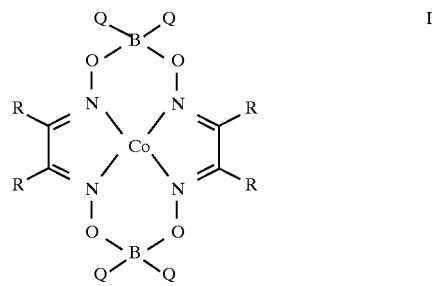

wherein each group R is an organic group and each group R is the same organic group as the other groups R, which group R is selected from (a) the group

wherein $R^1$ is a $C_{1-12}$ alkoxy group; and (b) the group

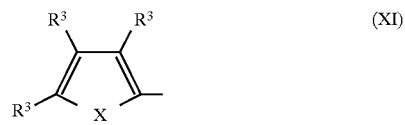

or corresponding compounds in which at least one of the 5-membered ring groups is joined at the 3-position instead of the 2-position (as shown above in XI) in which case $R^3$ is attached to a 2-position;

wherein each $R^3$ is selected, independently, from hydrogen, $C_{1-12}$ alkyl, optionally substituted $C_{6-10}$ aryl, OH, $OR^2$, $NH_2$, $NHR^2$, $NR^2_2$, $SO_3H$, $SO_3M$ where M is a cationic radical, $SO_3R^2$, $SO_2NH_2$, $SO_2NHR^2$, $CO_2H$, $CO_2R^2$, $NO_2$, CN, C(=O)H, C(=O)$R^2$, halogen, SH, and $SR^2$, wherein $R^2$ is a $C_{1-12}$alkyl or $(CH_2CH_2-O-)nT$ where n is 1 to 40 and T is H or a capping group selected from $C_{1-10}$ alkyl, $C_{1-11}$ aryl and (meth)acryloyl and wherein each X is selected, independently from O, S, NH and $NR^4$ where $R^4$ is $C_{1-6}$ alkyl, $C_{6-10}$ aryl or $C_{6-10}$ cycloalkyl, and each group Q is independently selected from F, Cl, Br, OH, $C_{1-12}$ alkoxy and $C_{1-12}$ alkyl.

7. A compound according to claim 6, wherein each Q is F.

8. A compound according to claim 6, wherein each group R is a group of the formula (X), given and defined in claim 6 and each $R^1$ is a $C_{1-2}$ alkoxy group.

9. A CoII chelate of the formula IV:

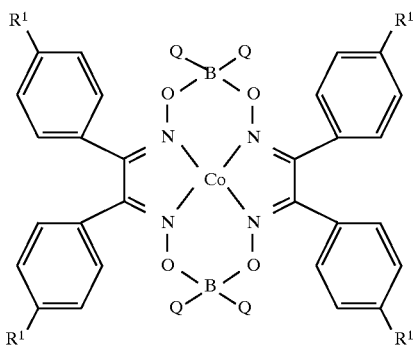

wherein each $R^1$ is a $C_{1-12}$ alkoxy group and each Q is independently selected from F, Cl, Br, OH, $C_{1-12}$ alkoxy and $C_{1-12}$ alkyl.

10. A process according to claim 5, wherein the CoII chelate has the formula VI:

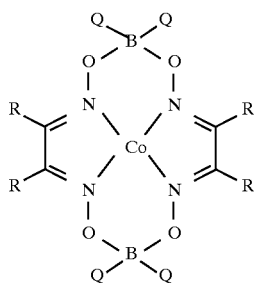

or a cobalt III analogue thereof.

11. A process according to claim 1 wherein the polymerization is carried out in the presence of a suspending agent.

12. A process according to claim 11, wherein the suspending agent is present in an amount of up to 8 g per 100 g of monomer.

13. A process according to claim 12, wherein the suspending agent is present in an amount of from 0.1 to 5 g per 100 g of monomer.

14. A process according to claim 1, wherein at least one said olefinically unsaturated monomer is a methacrylic monomer.

15. A CoII chelate of the following formula I:

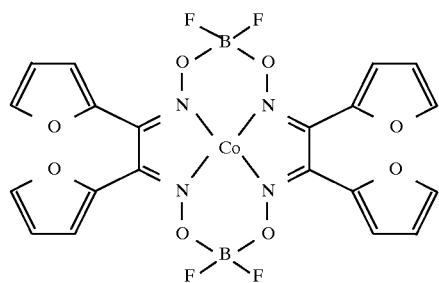

wherein each group R is an organic group which, independently, is a monovalent group which comprises a cyclic structure or taken together as two adjacent groups provides a divalent group completing a cyclic structure with the adjacent carbon atoms, and wherein further at least one of the groups R includes at least one heteroatom selected from O, N, S, P, halogen and Si, which heteroatom provides a substituent group or part of a substituent group on the cyclic structure, or a heteroatom of a heterocyclic ring of the cyclic structure; and wherein each group Q is independently selected from F, Cl, Br, OH, $C_{1-12}$ alkoxy and $C_{1-12}$ alkyl; or being a CoIII analogue of the cobalt II chelate of formula I in which the Co atom is additionally covalently bonded to H, a halide or other anion, or a homolytically dissociable organic group.

16. A CoII chelate of the formula

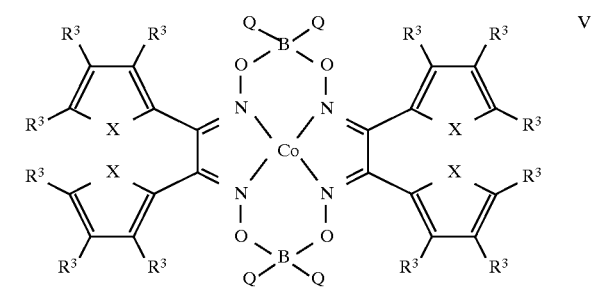

or corresponding compounds in which at least one of the 5-membered ring groups is joined at the 3 position instead of the 2 position (as shown above in V) in which case $R^3$ is attached to a 2-position;

wherein each $R^3$ is selected, independently, from hydrogen, $C_{1-12}$ alkyl, optionally substituted $C_{6-10}$ aryl, OH, $OR^2$, $NH_2$, $NHR^2$, $NR^2_2$, $SO_3H$, $SO_3M$ where M is a cationic radical, $SO_3R^2$, $SO_2NH_2SO_2NHR^2$, $CO_2H$, $CO_2R^2$, $NO_2$, CN, C(=O)H, C(=O)R, halogen, SH, and $SR^2$, wherein $R^2$ is a $C_{1-12}$ alkl or $(CH_2C_2—O)nT$ where n is 1 to 40 and T is H or a capping group selected from $C_{1-10}$ alkyl, $C_{1-11}$ aryl and (meth)acryloyl and wherein each X is selected, independently from O, S, NH and $NR^4$ where $R^4$ is $C_{1-8}$ alkyl, $C_{6-10}$ aryl or $C_{6-10}$ cycloalkyl, and each group Q is independently selected from F, Cl, Br, OH, $C_{1-12}$ alkoxy and $C_{1-12}$ alkyl.

17. A CoII chelate of the formula VI:

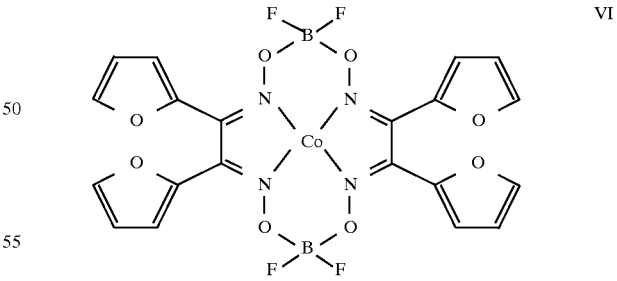

* * * * *